(12) United States Patent
Edirisuriya et al.

(10) Patent No.: US 6,953,354 B2
(45) Date of Patent: Oct. 11, 2005

(54) CONNECTOR FOR BREATHING CONDUITS

(75) Inventors: Deshitha Airawana Edirisuriya, Auckland (NZ); Kristopher Poh Ming Laurent, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/452,448

(22) Filed: Jun. 2, 2003

(65) Prior Publication Data
US 2003/0236015 A1 Dec. 25, 2003

(30) Foreign Application Priority Data
Jun. 5, 2002 (NZ) .............................................. 519374

(51) Int. Cl.[7] .................................................. H01R 4/60
(52) U.S. Cl. ...................................... 439/191; 439/352
(58) Field of Search ............................... 439/191–195, 439/350–358

(56) References Cited

U.S. PATENT DOCUMENTS

| | | | |
|---|---|---|---|
| 4,639,055 A | * | 1/1987 | Keane ......................... 439/192 |
| 4,787,117 A | * | 11/1988 | Westergren ................... 15/339 |
| 4,826,444 A | * | 5/1989 | Genoa et al. ................. 439/191 |
| 5,387,117 A | * | 2/1995 | Moyher et al. ............... 439/191 |
| 5,392,770 A | | 2/1995 | Clawson et al. |
| 5,537,996 A | | 7/1996 | McPhee |
| 5,637,006 A | * | 6/1997 | Almeras ....................... 439/191 |
| 5,640,951 A | | 6/1997 | Huddart et al. |
| 5,658,159 A | * | 8/1997 | Gardner et al. .............. 439/294 |
| 5,980,289 A | * | 11/1999 | Engle ........................... 439/195 |
| 6,078,730 A | | 6/2000 | Huddart et al. |
| 6,464,520 B2 | * | 10/2002 | Saba ............................. 439/191 |
| 6,705,478 B1 | * | 3/2004 | Engle ............................ 213/1.3 |
| 2003/0059213 A1 | | 3/2003 | Mackie et al. |

FOREIGN PATENT DOCUMENTS

| | | |
|---|---|---|
| DE | 19725875 | 12/1998 |
| DE | 19958296 | 9/2001 |
| EP | 1145678 | 1/1995 |
| EP | 1127583 | 8/2001 |
| EP | 1166814 | 1/2002 |
| GB | 2056611 | 3/1981 |
| WO | WO 02/32486 | 4/2002 |

* cited by examiner

*Primary Examiner*—Gary Paumen
(74) *Attorney, Agent, or Firm*—Trexler, Bushnell, Giangiorgi, Blackstone & Marr, Ltd.

(57) ABSTRACT

The present invention relates to the connections between respiratory humidifiers and/or other such devices and heated breathing conduits used to couple a patient to the humidifier. In particular, the invention is a connector to couple a gases supply means and a conduit, such that the connector causes there to be an electrical and pneumatic, that is, sealed connection between a conduit including an electrical wire extending within, throughout or about it and a gases supply device, such as a humidifier, blower or the like. The connector may be of a single port type or a dual port type. The dual port type connector is suitable for ventilator apparatus that have a dry line (dry breathing conduit) extending from a ventilator or blower that carries dry gas to a humidifier and an inspiratory limb that extends from the humidifier to the patient and carries humidified gases to the patient.

11 Claims, 18 Drawing Sheets

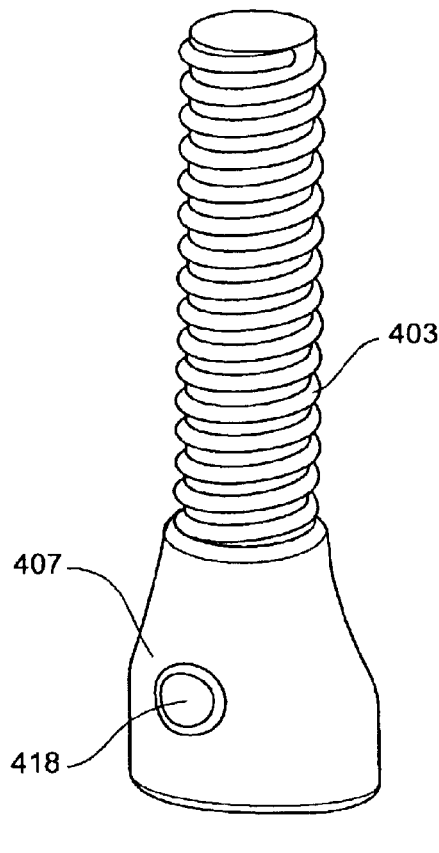
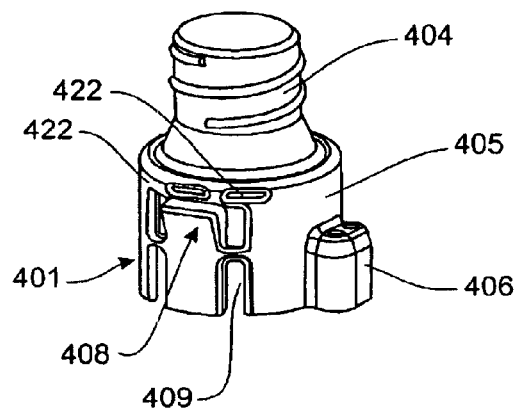
FIGURE 18  FIGURE 19
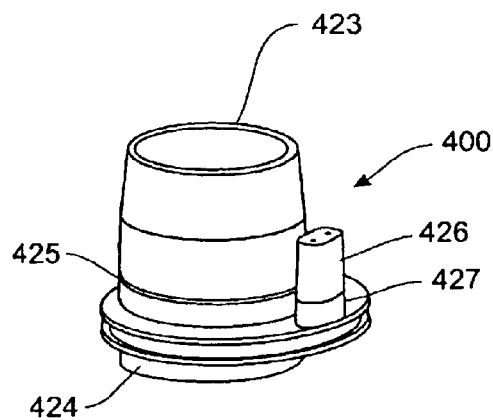
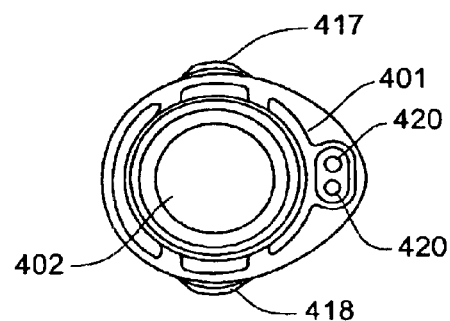
FIGURE 20  FIGURE 21

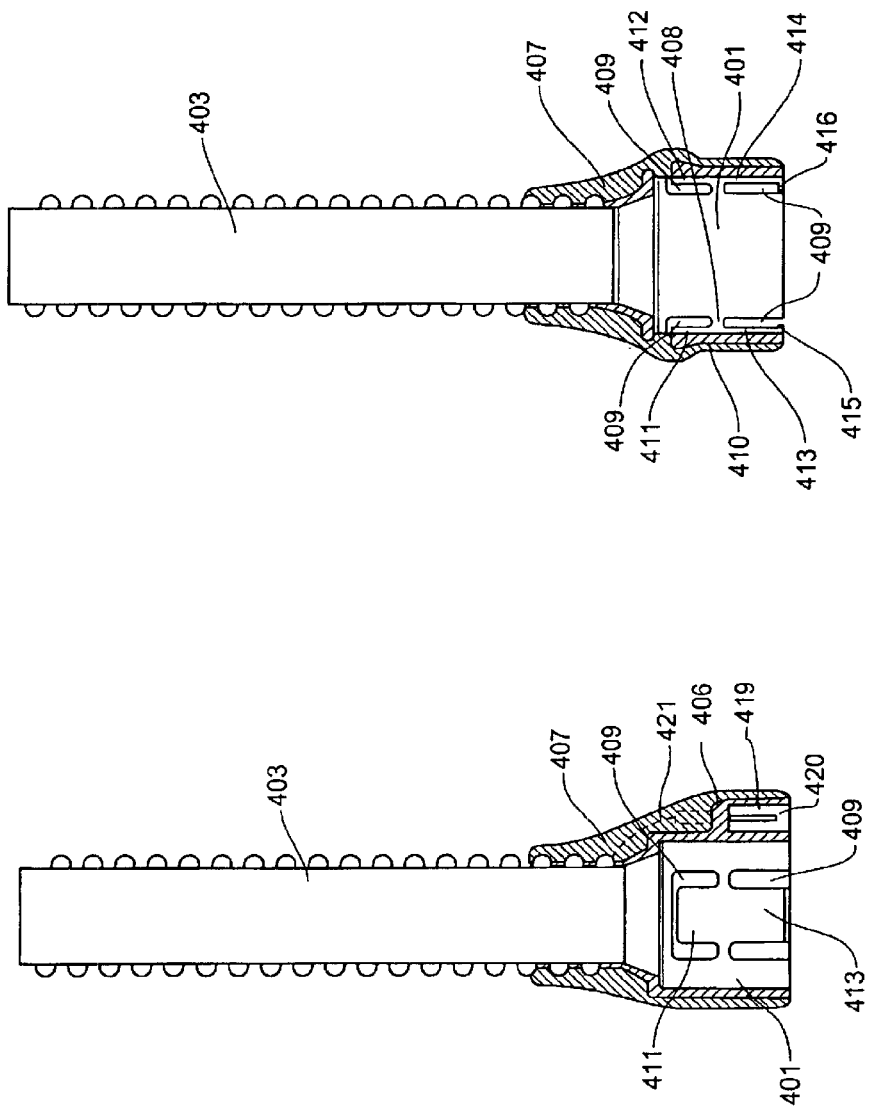

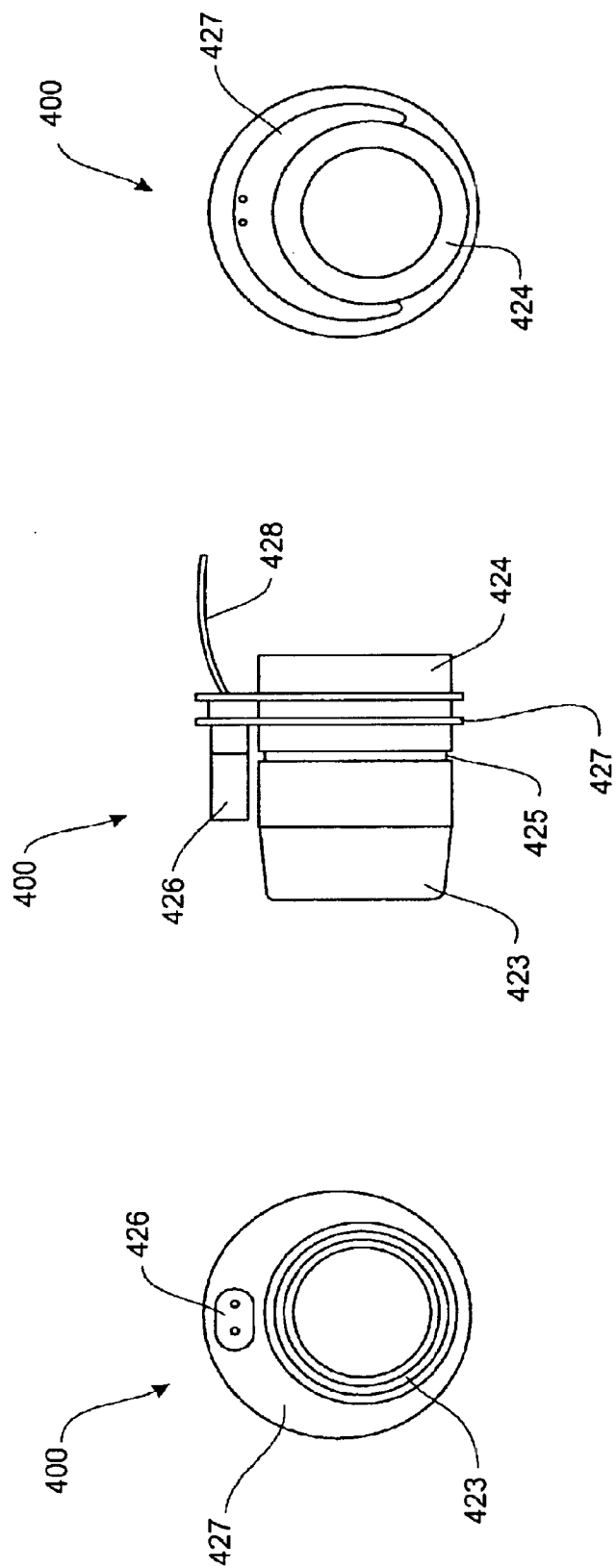

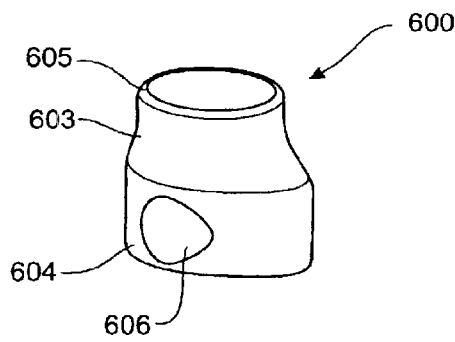
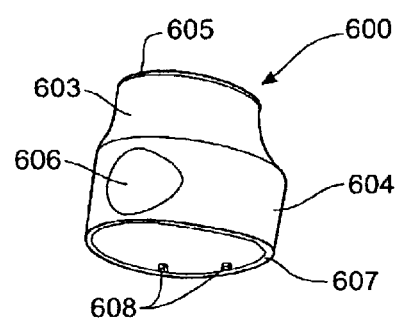
FIGURE 29  FIGURE 30
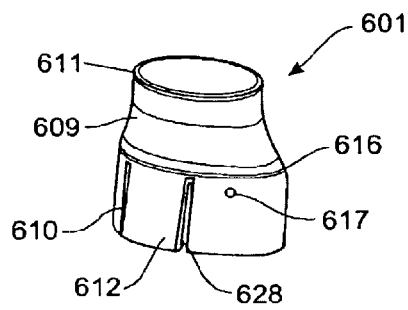
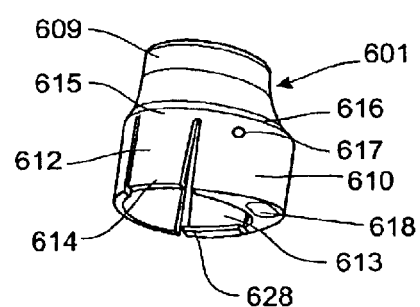
FIGURE 31  FIGURE 32

CONNECTOR FOR BREATHING CONDUITS

FIELD OF INVENTION

The present invention relates particularly, though not solely, to the delivery of humidified pressurised oxygen and/or air to a patient. In particular, the present invention relates to the connections between respiratory humidifiers and other such devices and heated breathing conduits used to couple a patient to the humidifier.

SUMMARY OF THE PRIOR ART

In order to supply gases to a patient or a person needing such gases, it may sometimes be necessary to first humidify those gases, for example using a respiratory humidifier/ventilator system. In such a case where the gases have been humidified, and therefore laden with water, it is likely that during transport through a conduit to the patient, condensation of that water vapour will occur. In order to overcome this disadvantage it is known to associate a heater wire with respiratory humidifier breathing conduits to avoid condensation. Examples of such a heated breathing conduit are disclosed in U.S. Pat. No. 5,537,996 (McPhee) and U.S. Pat. No. 5,392,770 (Clawson et al.). A connector that simply fits into the humidifier chamber outlet is currently known that provides for connection between a humidifier and a breathing conduit. FIG. 1 illustrates how current is supplied to the heater wire within the breathing conduit and the connection between the conduit and humidifier. The humidifier 102 has a humidification chamber 103 having an inlet 104 that is connected to the outlet of a device that supplies gases to the humidifier. The humidification chamber 103 also has an outlet 105. A connector 106 connects the breathing conduit 101 and the outlet 105. The connector 106 is located at one end of the conduit 101. The end of the connector 106 fits snugly into or about the outlet 105. The wire within the breathing conduit 108 is heated by way of the external connector 109 that is connected via electrical wiring to the humidifier base 110.

Existing connectors of this type have the disadvantage that there are external wires that may cause problems for the user and will be in the way when in use.

A further disadvantage of connectors of this type is that connection and disconnection is frequent in use, to replace contaminated parts or similar. It is awkward to repeatedly release and reconnect separate electrical and pneumatic conduits, especially as prior art devices usually require the use of both hands in order to securely establish or remove the connections.

Furthermore, the connection between the breathing conduit and the humidifier outlet does not provide an optimal connection.

In order to overcome this problem, connectors that make both a pneumatic and an electrical connection are often used. Examples of connectors of this type are disclosed in DE 19958296 and EP 1127583 where both an electrical and a pneumatic connection are made by connecting a male connecting part and a female connecting part by a simple push-fit connection. More robust connections can be made, such as that disclosed in DE 19725875, where a motor is used to drive a spindle into a receiver such as a nut, in order to achieve a pneumatic and electrical connection and to securely hold the male and female parts together.

Another mechanism for securely holding a male part and a female part together is disclosed in EP 1145678, where a pivoting hook on the male portion releasably locks the male portion to the female portion.

SUMMARY OF THE INVENTION

It is an object of the present invention to provide a connector between a gases supply means and a heated breathing conduit that goes some way towards overcoming the abovementioned disadvantages.

In a first aspect the present invention consists in a connector for coupling a gases supply to a conduit, where said conduit is of the type that includes electrical wire extending within, throughout or about said conduit, said connector comprising:

a female gases passage portion of a generally tubular shape attached in use to one of said gases supply or said conduit, said female portion including a locking connector and an electrical connector.

a male gases passage portion of a generally tubular shape attached in use to the other of said gases supply or said conduit, said male gases passage portion including a locking connector receiver and an electrical connector receiver, said male gases passage portion and said female gases passage portion coupled in use to form a pneumatically sealed gases passage between said gases supply and said conduit, said coupling also engaging said electrical connector and said electrical connector receiver, the improvement comprising:

a collar of generally tubular shape on said female portion, said collar capable of being moved over said female gases portion once said male and female gases passage portions are coupled in use, said collar causing said locking connector to engage with said locking connector receiving to releasably lock said male and female portions together.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which;

FIG. 18 is a perspective view of the male as moulded to one end to a conduit according to a portion as third form of the present invention, FIG. 19 is a perspective view of the male portion of FIG. 18 when not moulded to the conduit, FIG. 20 is a perspective view of the female portion of the connector according to a third form of the present invention, FIG. 21 is a underneath view of the male portion of the connector of the third form of the present invention, FIG. 22 is a cross-sectional side view of the male portion of FIG. 18, FIG. 23 is an alternative side cross-sectional view of the male portion of FIG. 19, FIG. 24 is a underneath view of the female portion of FIG. 20, FIG. 25 is a side view of the female portion of FIG. 20, FIG. 26 is a plan view of the female portion of FIG. 20.

FIG. 29 is a first perspective view of a sliding cover of a connector according to fourth form of the present invention, FIG. 30 is a second perspective view of the sliding cover of FIG. 29, FIG. 31 is a first perspective view of the female portion according to the fourth form of the connector of the present invention, FIG. 32 is a second perspective view of the female portion of FIG. 31.

DETAILED DESCRIPTION OF THE PREFERRED EMBODIMENTS

Figure 1:
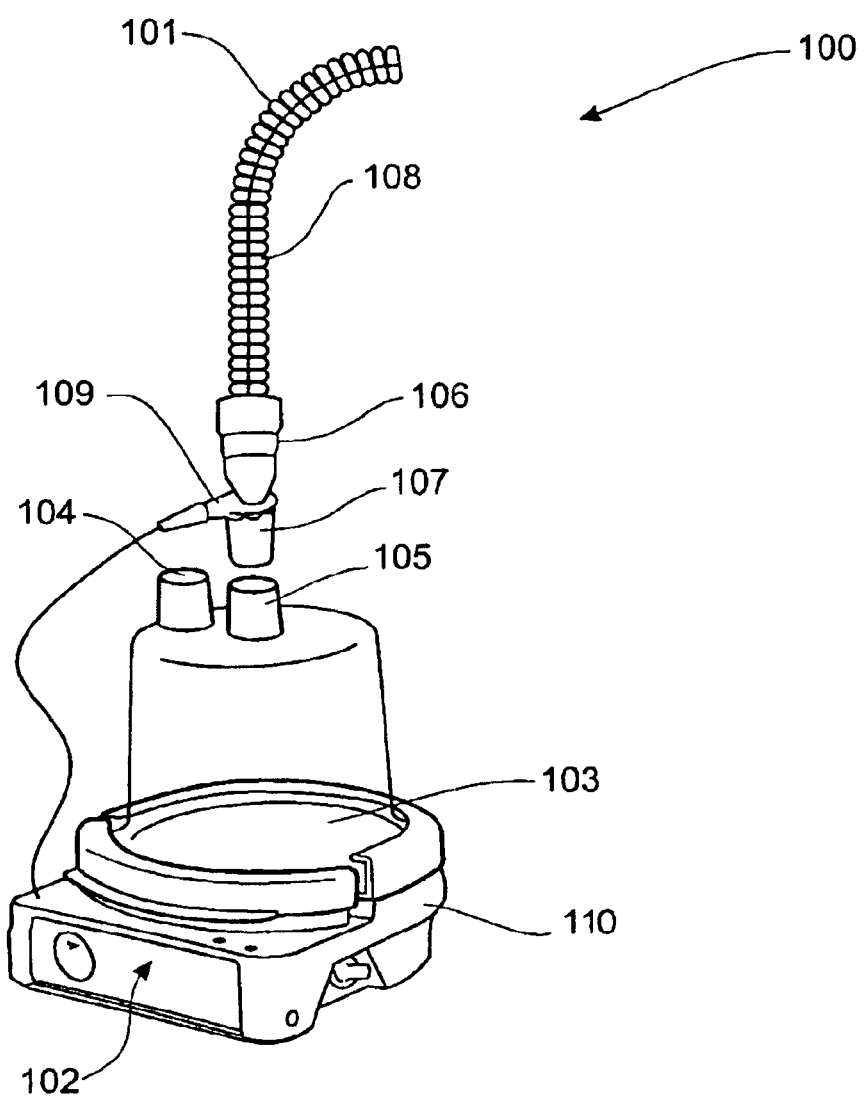
FIG. 1 is a connector used in prior art devices to provide the connection between a breathing conduit and humidifier.
Figure 2:
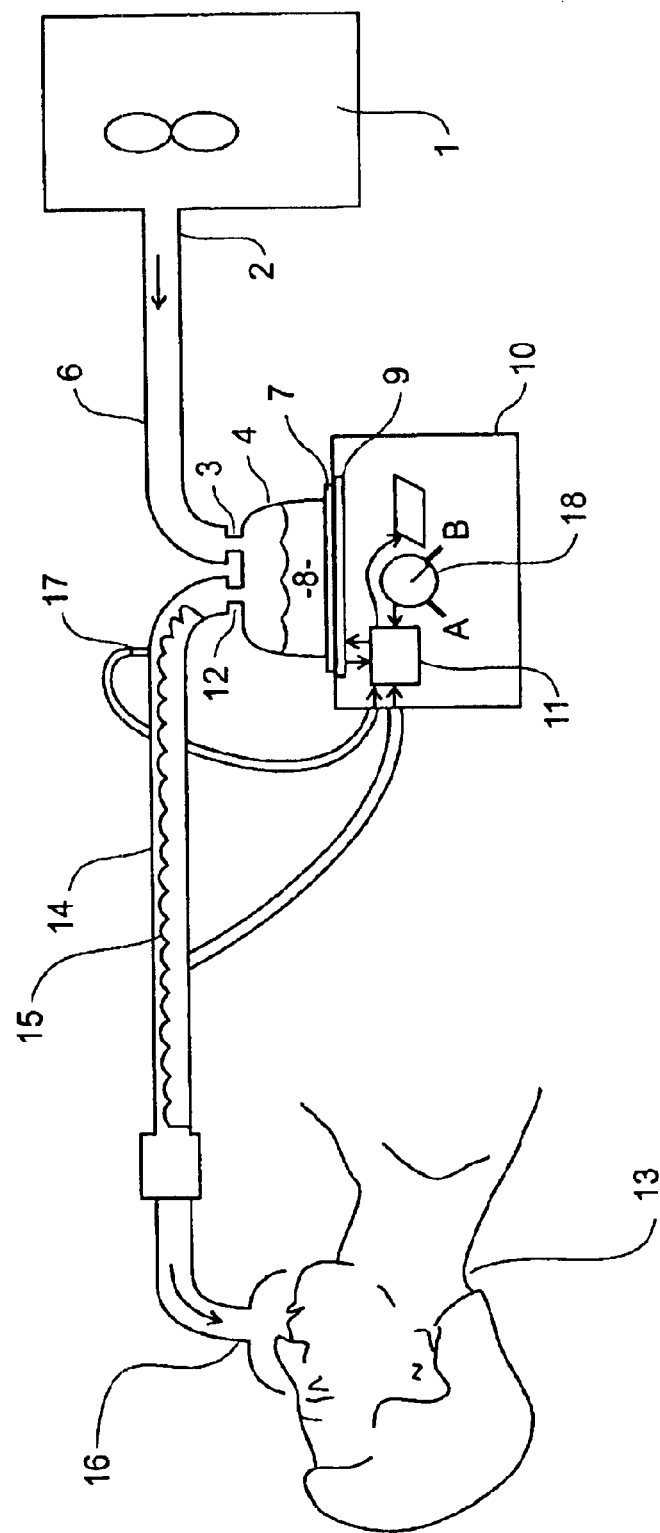
FIG. 2 is a schematic diagram of a respiratory humidification system that may incorporate the detection of conduit overheating system of the present invention.

With reference to the accompanying drawings and in particular to FIG. 2, an example of a humidification apparatus and respiratory humidification system incorporating preferred embodiments of the connector of the present invention is illustrated. In the description below, reference has been made to the connection of a breathing conduit to a humidifier. It, must be appreciated that the connector of the present invention may be used to connect a breathing conduit to other medical devices, such as positive pressure ventilation devices, continuous positive airway pressure (CPAP) devices, insufflation devices, integrated insufflation and humidification devices, integrated CPAP and humidifier devices, or any other such breathing assistance device that can be used in either home-care or hospital applications. The use of the word humidifier alone must not be seen as restrictive to the application or use of the connector of the present invention.

Included in the example respiratory humidification system as shown in FIG. 2, is a gases supply means 1, such as a ventilator or blower, having an outlet 2 that supplies gases (for example oxygen, anaesthetic gases or air) to the inlet 3 of a humidification chamber means 4 via a conduit 6. Humidification chamber means 4 may, for example, comprise a plastics formed chamber having a metal base 7 sealed thereto. Humidification chamber 4 is adapted to hold a volume of water 8, which is heated by a heater plate means 9 under the control of controller or control means 11 of a humidification device or humidifier 10.

As the water within chamber 4 is heated it will slowly evaporate, mixing water vapour with the gases flow through the humidification chamber from ventilator 1. Accordingly, humidified gases leave the humidification chamber 4 via outlet 12 and are passed to a patient or other person in need of such gases 13 through a gases transportation pathway or inspiratory conduit 14. The conduit 14 is connected to the outlet of the humidifier chamber by way of a connector that will be described below. In order to reduce condensation within the inspiratory conduit 14 and to raise the temperature of the gases provided to the patient 13 a heating wire means 15 is provided which is energised under the control of control means 11.

Figure 3:
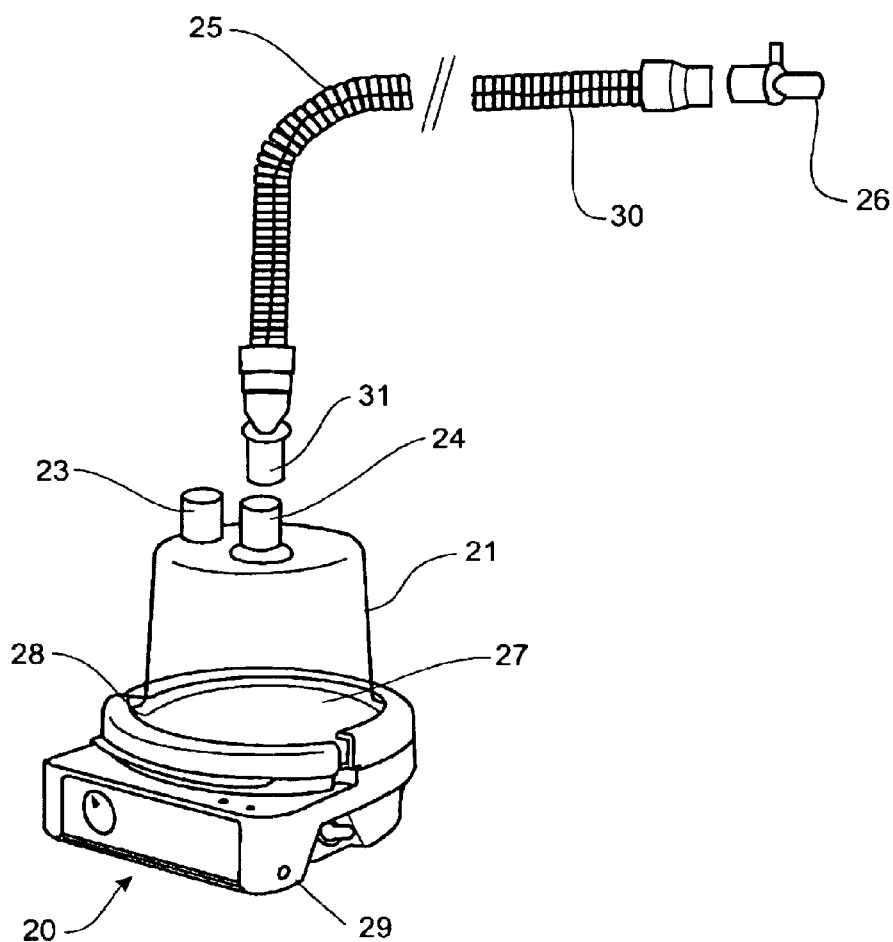
FIG. 3 is an illustration of a respiratory humidifier system that utilises the connector of the present invention.
Figure 4:
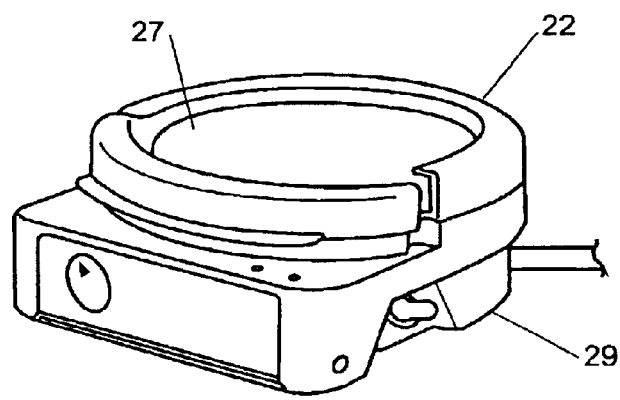
FIG. 4 is an illustration of the humidifier base of the respiratory humidifier system of FIG. 2.

With reference to FIGS. 3 and 4, which show the humidifier 10 of FIG. 2 in more detail, the humidifier 20 has a humidifying chamber 21 having edges; which engage with collar 22 on the humidifier 20. The gases to be humidified may be a mixture of air, oxygen and anaesthetic for example, which are supplied to the chamber through gas inlet 23. This might be connected to a ventilator, a source of pressurised oxygen, a flow generator, or air compressor. A gases outlet 24 is also provided and the gases outlet 24 is connected to the conduit 25, which conveys humidified gases to the patient at the end 26 of the conduit. The end 26 of the conduit may have a cannula connected to the patient's nose, a nasal mask, or a facemask connected to the user's face, so as to supply humidified gases to the user. The humidifier heater plate 27 has a temperature transducer 28 that is in electrical connection with the electronic control circuitry in body 29 of the apparatus so that the control means monitors the temperature of the heating plate.

A heating element 30 is provided within the conduit 25 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the gases through conduction and convection during transit through the conduit. Thus the conduit heater element ensures the gases delivered are at an optimal temperature and humidity.

The end of the conduit 25 has a connector 31 suitable for coupling the conduit to the humidifier. The connector comprises a male portion attached to the humidifier and a female portion attached to the breathing conduit, which when coupled provides both a pneumatic and electrical coupling between the humidifier chamber and breathing circuit. The effect of the electrical connection in this manner, is that the electrical wire running the length of the conduit is controllable from the humidifier without there being additional external wiring from the humidifier to the conduit that could be accidentally removed by a patient or user. The connector is described in more detail below.

Integrated Gases Supply Means and Humidifier Apparatus

Figure 5:
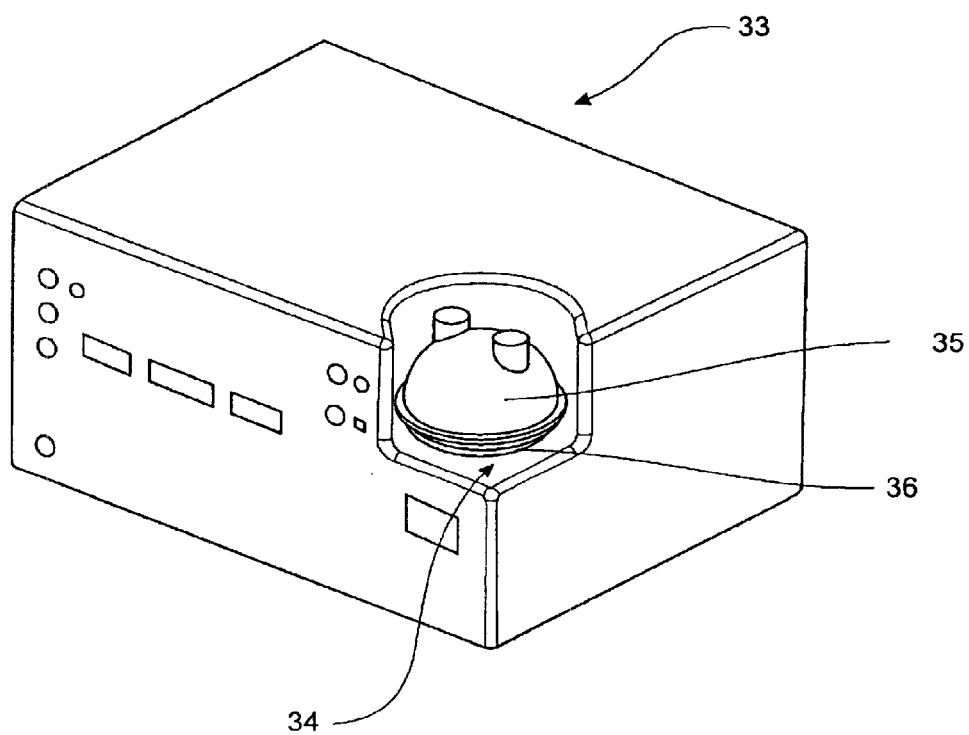
FIG. 5 is a perspective view of apparatus that is used in conjunction with the connector of the present invention, wherein the gases supply means and humidifier are contained within an enclosure.

In an alternative application, the connector of the present invention may be used with a humidifier that has been integrated with a gases supply means as shown in FIG. 5. The gases supply means (such as a blower, ventilator or insufflator) and humidifier are housed within an enclosure 33. The enclosure 33 has a recess 34 that provides an area for a humidifying chamber 35 to be located in. The chamber 35 is situated upon a heater plate 36, which is connected to electronics that heat the plate 36, and enables humidification of the gas within the chamber when the chamber has water placed within it.

Figure 6:
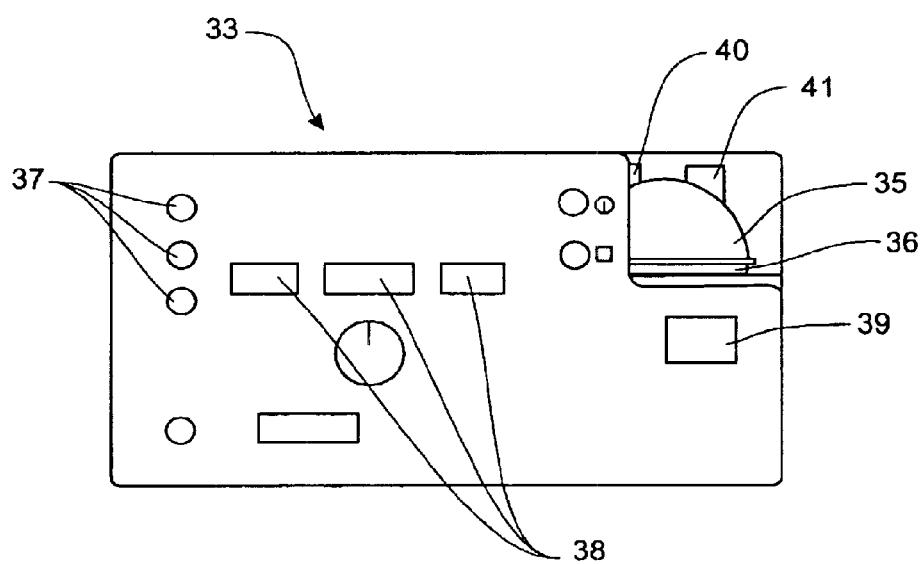
FIG. 6 is a front view of the apparatus of FIG. 5.

Referring now to FIG. 6, the chamber 35 has an entry port 40 that is connected to the outlet of the gases supply means housed within the enclosure 33, and an exit port 41 that has connected to it the breathing conduit (see FIG. 7) that carries the gas to the patient.

Figure 7:
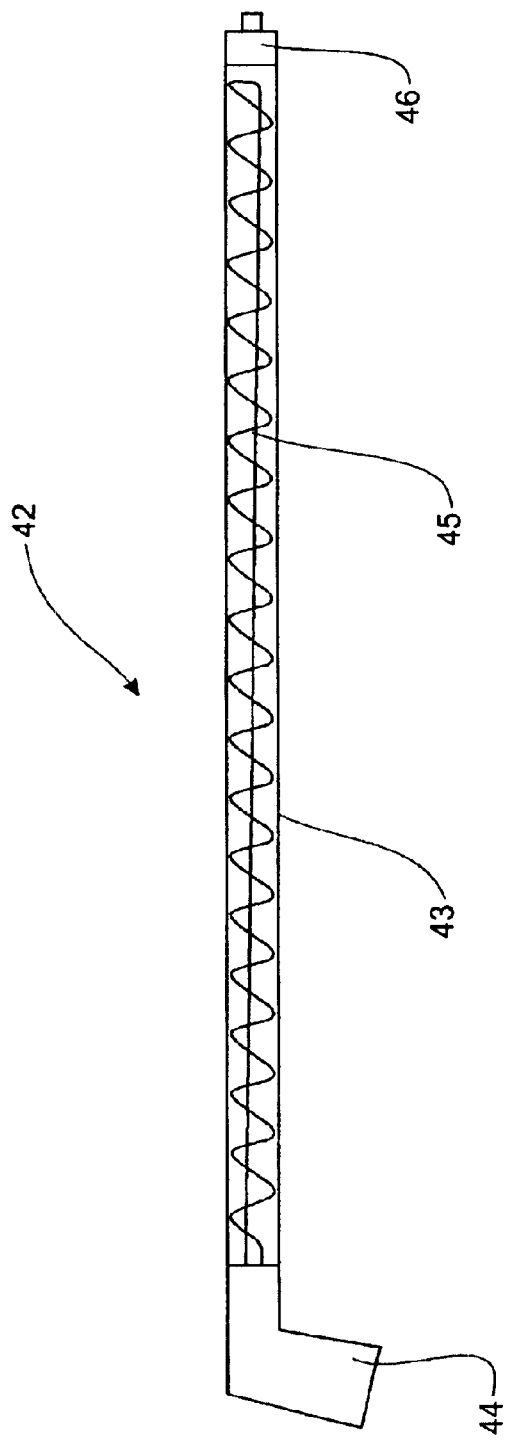
FIG. 7 is a side view of the heated gas delivery system as connected to the connector of the present invention.

External to the enclosure is the breathing conduit, which is shown in FIG. 7. This takes warm, humid gas from the enclosure and delivers it to the patient, maintaining temperature and humidity of the gas. The conduit 42 comprises a tube 43, connector 44, spiral wire 45 and end 46, for use to connect the breathing conduit to the patient.

The enclosure end of the tube has a connector 44 suitable for connecting to the gas outlet of the humidifier and an electrical socket suitable for connecting to the electrical outlet of the humidifier (not shown) within the enclosure 33. The connector 44 and electrical socket are described in more detail below. Within the tube 43 is a spiral wound heater wire 45, such as that described in U.S. Pat. No. 5,640,951 or U.S. Pat. No. 6,078,730 (Fisher & Paykel Limited) running inside part of, or all of the length of the tube 43. The terminations of this heater wire are connected to the electrical socket of the connector 44.

Single Port Electrical/Pneumatic Connector

The connector of the present invention in a first form is a single port connector, which provides the connection between a humidifying apparatus and a breathing conduit with integral heating wire, such as described above. The connector comprises a male portion attached to a humidifier chamber and a female portion attached to the heated breathing circuit so that in use when the male and female portions are coupled together, a pneumatic and an electrical coupling is achieved between the breathing circuit and humidifier or other such device, such as a positive pressure ventilation device or blower.

Figure 8:
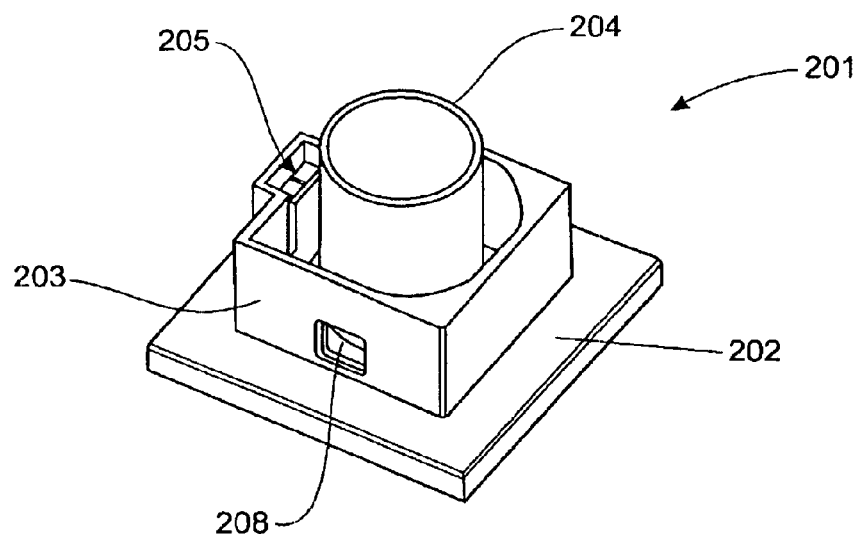
FIG. 8 is a perspective view of the male portion of a first form connector of the present invention, where the connector has a single port.
Figure 9:
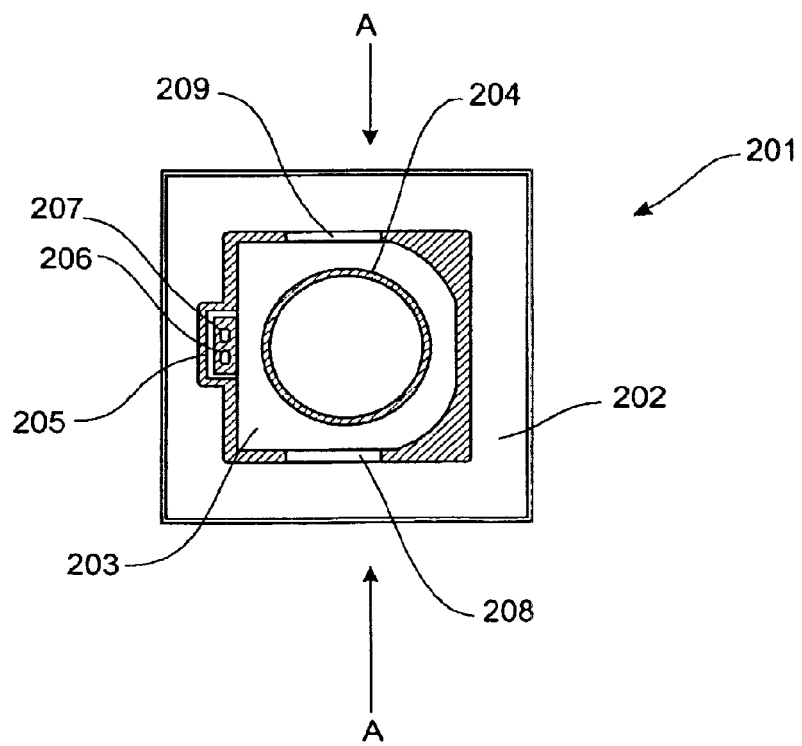
FIG. 9 is a plan view of the male portion of the connector of FIG. 8.
Figure 10:
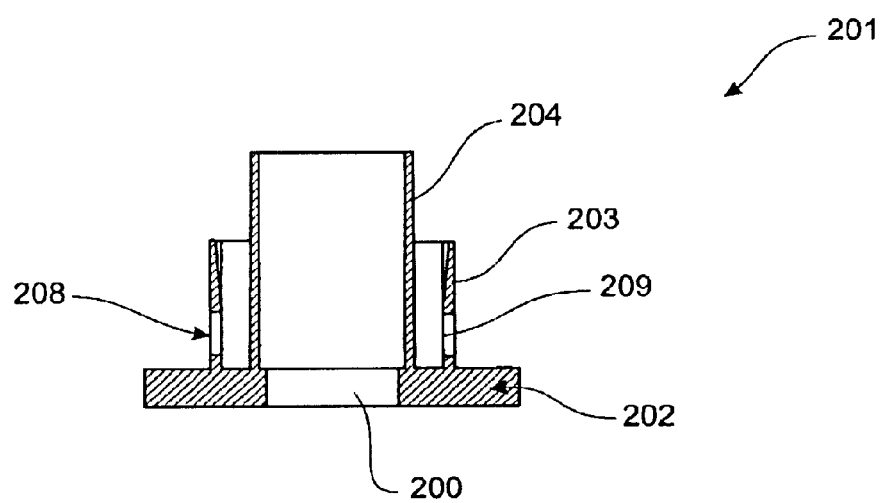
FIG. 10 is a side cross-sectional view of the male portion of the connector of FIG. 7.

The male portion of the first form of a connector in accordance with the present invention is shown in FIGS. 8 to 10. The male portion 201 of the connector is generally tubular in shape, having a base 202 that is attached, in an appropriate manner, to the chamber of the humidifying apparatus. In some forms of this connector the base 202 will be the body of the humidifying chamber itself, but in other forms the base may be clipped, welded, moulded or otherwise appropriately attached to the chamber or base of the humidifier. The male portion itself is separately injection moulded, but may be moulded so as to be integral with the humidifier chamber. If desired, the mechanism that provides the pneumatic sealing between the humidifier and the conduit can be separately attached to the chamber of the humidifier, and freely removable, with sealine achieved by an O-ring or other appropriate means when the conduit is connected to the humidifier.

Extending from the base 202 of the male portion is the body 203 and further extending from the base 202 and within the body 203 is a tubular protrusion 204. As can be seen in FIG. 10 the tubular protrusion 204 extends through the body section 202 and abuts the circular recess 200 located in the base of the male portion, in order to allow gases to flow through the male portion from the chamber.

Located on the body of 203 of the male portion is an electrical socket 205 having conductors 206, 207. On opposed walls of the body 203 there are two elongate apertures 208, 209 that serve to receive complimentary protrusions 213, 215 on the female portion, so that when the male and female portions are coupled, part of each of the protrusions 213, 215 will reside within the apertures 208, 209 on the male portion, causing a pneumatic seal to be formed between the two parts.

In use, gases flow from the humidifying chamber through the recess 200 into the tubular protrusion 204 then into the female portion 210 of the connector attached to the breathing conduit, and finally through into the breathing conduit to the patient.

Figure 11:
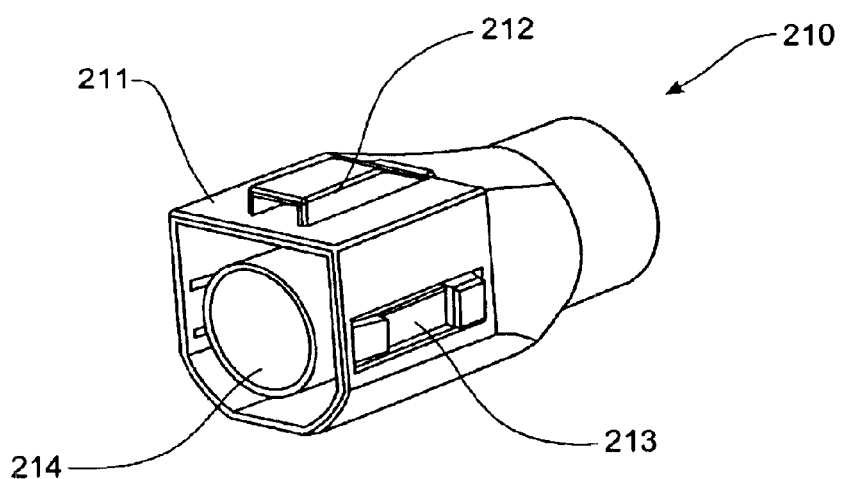
FIG. 11 is a perspective view of the female portion of the first form of the connector of the present invention.
Figure 12:
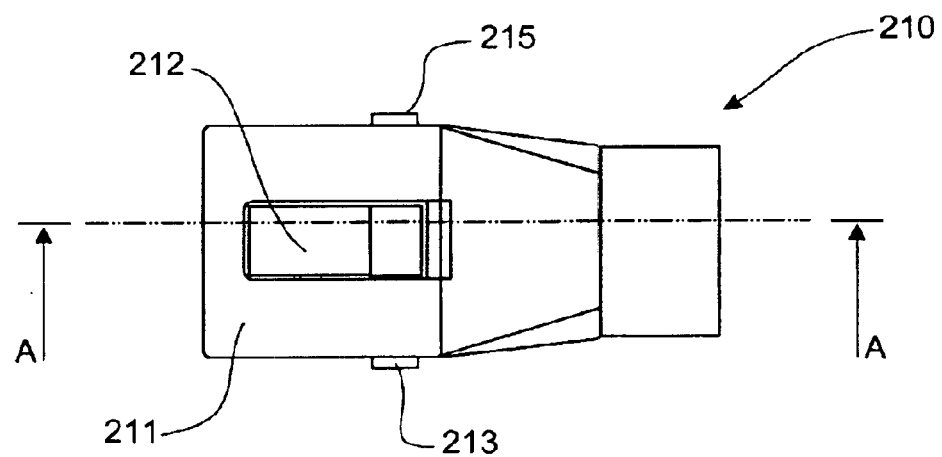
FIG. 12 is a plan view of the female portion of the connector as shown in FIG. 9.
Figure 13:
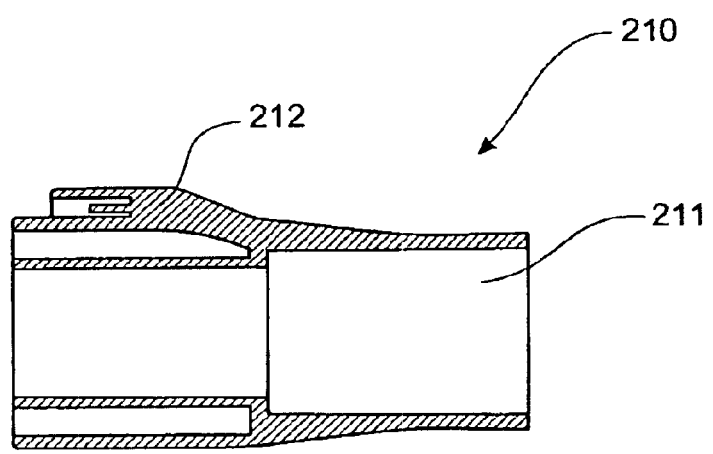
FIG. 13 is a cross-sectional view of the female portion of the connector shown through A—A in FIG. 10.

The female portion of the connector will now be described in greater detail with reference to FIGS. 11 to 13. The female portion 210 is a generally tubular member that is attached about or within the breathing conduit (not shown) in an appropriate manner. The female portion 210 is manufactured by injection moulding from a plastics material but other appropriate methods of manufacture or materials may be used. The female portion 210 comprises a sleeve 211 having an electrical port 212 and protrusions 213, 215 located on either side of the outer wall. Extending within the sleeve 211 is a port 214 that is also tubular in shape. The electrical port 212 has pins or contact surfaces located within it (not shown) that are connected to the heater wire 45 (as already described) residing within or about the breathing conduit. Soldering or fastening the heater wire 45 to the pins or contact surfaces by appropriate fastening means causes connection from the electrical port 212 to the heater wire 45. The pins or contact surfaces can be either moulded into the port 212 during the moulding of the female portion, or may be inserted into the port 212 during moulding.

When the male portion 201 and female portion 210 are coupled the tubular protrusion 204 of the male portion 201 slides between the tubular port 214 and the sleeve 211 on the female portion 210. Simultaneously the protrusions 213, 215 slot into the apertures 208, 209 and the electrical port 212 fits into the socket 205. Thus the meeting of the male and female portion achieves a simultaneous electrical and pneumatic connection to be made.

The protrusions 213, 215 and apertures 208, 209 also have the effect of providing a quick release mechanism that allows user-friendly and efficient release of the circuit from the humidifier. When a user wishes to remove the male portion from the female portion they need only push the protrusions 213, 215 inward releasing them from the apertures 208, 209 and then remove the male portion from within the female portion.

In further forms of the connector as described above, a taper may be provided on the inner walls of the female or male portions and a gasket placed in between the two surfaces. Alternatively, a thread or a bayonet type fitting could be used to create the pneumatic seal instead of the taper and/or quick release mechanism described above.

The conductors 206, 207 referred to above may be assembled with the male portion 201 and then over-moulded, or may be inserted into the electrical socket 205 on the male portion 201 after portion has been moulded. Alternatively, a separate sub assembly with the conductors 206, 207 could be formed and threaded onto the conduit, and then over-moulded.

In preferred forms of the present invention, a small indicator, such as an LED (not shown), is embedded in either the male or female portion of the connector to allow for visual confirmation of an active circuit, so as to indicate both an electrical connection and a pneumatic seal.

The heater wire 45 located within the breathing conduit could also be accompanied by at least one additional electrical lead that can carry signals from measuring sensors placed at the ends of, or at intermediate positions along the conduit. Furthermore, the heater wire 45 itself could be used to carry electrical signals from measuring sensors. When additional leads are supplied additional pins and/or contacts are supplied within the electrical.

A second form of a "single port" connector according to the present invention is shown in FIGS. 18 to 26. This connector is comprised of a generally tubular shaped male portion 400 and similarly shaped female portion 401, where the male portion is fittable within the female portion. Referring to FIGS. 18, 19, 22 and 23 it can be seen that the female portion 401 has a tubular pathway 402 through it, to allow gases to pass through the portion 401 into the conduit 403. The female portion 401 is a thermoplastic insert that has a body section 405 and a threaded end 404 that is of a reduced diameter compared to the body section 405. The body section 405 has a hollow protrusion on its outside surface, that defines an electrical recess or electrical port 406 when the female portion is moulded to the conduit 403. The electrical port 406 is of generally rectangular cross-section and shape and extends along the outer surface of the body section 405.

The insert 401 is attached to the conduit 403 by threading the conduit about the end 404. The conduit and insert 401 are then over-moulded. A number of recesses 422 located on the outer surface edge of the insert 401 (nearest the threaded end 404) allow the plastics material used for moulding (such as a thermoplastic elastomer) to flow into the insert 401, forming a gasket. After this over-moulding process the plastics material from the moulding forms an outer surface covering 406 of thermoplastic elastomer over the end of the conduit 403 and the insert 401.

Additionally, at least one pivot catch or lock 408 is integrally formed in the polycarbonate body section 405 of the insert 401. The pivot lock or locks 408 are formed from a portion of the standard tubular shape of the body section, and are defined by pairs 01 channels 409 cut end to end from the body section, leaving a central bridging member. In cross-section as shown in FIG. 23, the body section has two pivoting members 408, 410. The thickness of the upper arms 411, 412 of the pivoting members increases nearer the top of the arms 411, 412, forming an outwardly extending protrusion from the surface of the body section 405. The lower arms 413, 414 have small inwardly extending protrusions 415, 416. These protrusions 415, 416 engage with the male portion of the connector 400, locking the male portion 400 and female portion 401 of the connector together when these are coupled. As can be seen in FIGS. 18, 21, 22 and 23, once the overmoulding of insert 401 and conduit 403 is completed, protuberances 417, 418 are formed in the outer covering 407 by the top edges of the upper arms 411, 412. The pivoting member 408 acts such that when the protuberances 417, 418 are pushed inwards the upper arms 411, 412 are moved inwards, pivoting about the bridging members and causing the lower arms 413, 414 and small protrusions 415, 416 to pivot outwards.

Referring to FIG. 22, before the over moulding of the insert and conduit is carried out, pins 420 are inserted into the recess 419 in the electrical port 406. Each of the pins is connected by appropriate means to the wires within the conduit. For example, each pin can be soldered to a connecting wire 421 and then the other end of this wire is soldered to the wires extending about or within the conduit. Again, this type of connection allows for power to be supplied to the conduit without externally running wires.

Reference is now made to FIGS. 20, 24, 25 and 26, which illustrate various views of the male portion 400 that couples with the female portion 401 of the alternative form of a single port connector of the present invention. The male portion 400 is generally tubular in shape, to allow gases to flow through the portion, but the diameter of the portion 400 decreases slightly, near the connection end 423, forming a tapering end on the portion 400. Partway along the portion 400 is a groove 425, spanning the circumference of the portion 400, in which the small protrusions 415, 416 on the female portion 401 fit or clip into when the connection end 423 of the male portion 400 is coupled to the female portion.

Located below the groove 425 is a rim 427, which prevents the male portion 400 from being pushed too far into the female portion 401. Located on one part of the oval shaped rim 427 is a rectangular shaped projection 426, forming an electrical connector, which houses elongate recesses that receive the pins 420, when the male and female portions are coupled. At the base of the elongate recesses is an electrical contact that is connected via standard wiring 428 to the power supply, usually retained within the humidifier control mechanisms.

In use, once the male portion 400 is attached to the humidifier and the female portion 401 moulded to the conduit 403, a connection is formed between the conduit 403 and the humidifier by coupling the male and female portions together. Once coupled, a pneumatic connection is made as the tubular body of the male portion fits within the tubular portion of the female body and the small protrusions 415, 416 clip into the groove 425, preventing removal of the male portion from the female portion. Simultaneously, the projection 426 on the male portion extends into the recess 419 in the electrical connector 406 on the female portion 401 and the pins 420 extend into the elongate recesses in the projection 426, thus an electrical connection is formed between the conduit wiring and the humidifier.

To remove the male portion from the female portion a user is simply required to apply pressure to the protuberances 417, 418 formed in the outer covering 407 of the female portion thereby releasing the small protrusions 415, 416 from the groove 425 on the male portion. The male portion can then simply be removed from within the female portion, thereby disconnecting the electrical connection between the two portions.

The male portion 400 is separately attached by appropriate means to the outlet of a humidifier chamber at the inlet end 424 of the male portion 400. In alternative embodiments, the male portion 400 may be formed integrally with the chamber of the humidifier, forming the outlet port of the chamber.

A third form of a "single port" connector according to the present invention is shown in FIGS. 29 to 36. A connector in this form is comprised of three parts, a sliding collar 600, a female portion 601 and a male portion 602, where the male portion is fittable within the female portion 601 and the sliding collar 600 slides over and about the female portion 601. The three parts, the sliding collar 600, the female portion 601 and the male portion 602, are generally tubular in shape to allow gases to pass through the tubular pathway formed between the male and female portions. Each of these portions is injection moulded in a plastics material, but other appropriate methods of manufacturing may be used. The sliding collar is preferably moulded from acetyl, and the male and female portions from polypropylene, but other appropriate materials such as other thermoplastic materials may be used.

The sliding collar as depicted in FIGS. 29 and 30 is of a generally tubular shape where the collar has two sections: an upper section 603, and lower section 604. The lower section 604 is oval in cross-section and tapers inwards (in a reducing diameter fashion) to the upper section 603 that becomes circular in cross-section at its edge 605. Located on the exterior surface of the lower section 604 are depressions 606 that are the shape and size of a human finger pad so that the depressions 606 form a gripping surface for a user's fingers. As shown in FIG. 30, on the interior surface of the lower section 604, on the lower edge 607 at least one but preferably two spaced apart small protrusions 608 are integrally moulded in the collar 600. These protrusions 608 slide within complimentary slots in the female portion 601 when the collar 600 is slid over the female portion 601.

Reference is now made to FIGS. 31 and 32, which depict the female portion 601 of the connector of the third form. The female portion 601 has upper and lower sections 609, 610 and is of a corresponding shape, but slightly smaller in diameter, to the sliding collar 600. Therefore, the upper section 609 reduces in diameter from the lower section 610 to an outer and upper edge 611. Integrally formed within the lower section are two pivoting members 612, 613, with free ends 614 on the lower part forming flexible members that are movable out of the plane of the sides of the lower section 610. The free ends 614 are moulded so that they protrude out of the surface of the lower section 610. The other ends 615 of the pivoting members 612, 613 are attached to the upper edge 616 of the lower section 610. The pivoting members 612, 613 are flexible and so allow the free ends 614 to be pushed inwards past the external surface of the female portion 601. Located on the surface of the lower section 610 is a dimple for aperture 617 that receives a complimentary shaped protrusion located on the inner surface of the sliding collar 600 when the collar 600 is slid over and about the female portion 601. Formed within the lower section 610 is a electrical port or recess 618 that houses pins as shown in FIG. 35, which will be described in more detail below.

Figure 36:
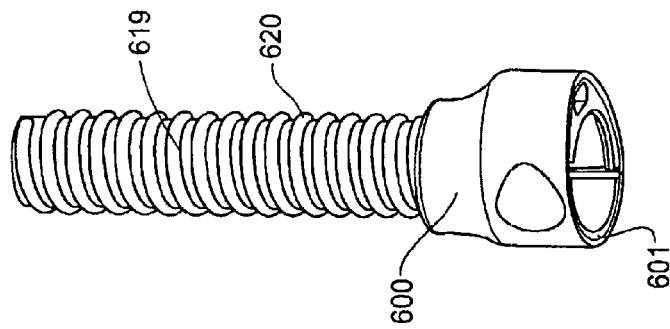
FIG. 36 is a perspective view of the breathing conduit, female portion and sliding cover as shown in FIG. 25.
Figure 35:
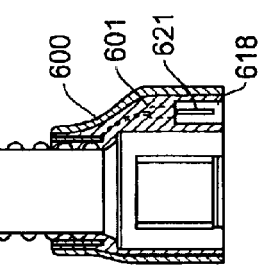
FIG. 35 is a cross-sectional view of the breathing conduit, female portion and sliding cover where the cover in a position that enables locking of the female portion to the male portion.
Figure 34:
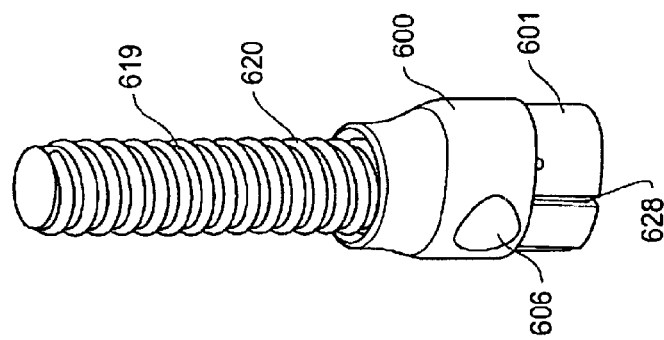
FIG. 34 is a perspective view of the breathing conduit attached to the female portion of the fourth form of the connector of the present invention, where the sliding cover is only partially covering the female portion.

The female portion 601 is moulded in a polypropylene or other appropriate plastics material over the tube 619 as shown in FIGS. 34 to 36. Referring to FIG. 35, during or before the moulding of the female portion 601 over the tube 619, the wires (that reside within the breathing conduit bead 620 encircling the conduit 619), are connected to standard wiring and subsequently to electrical pins 621 residing within the recess or port 618 formed during the moulding process.

Figure 33:
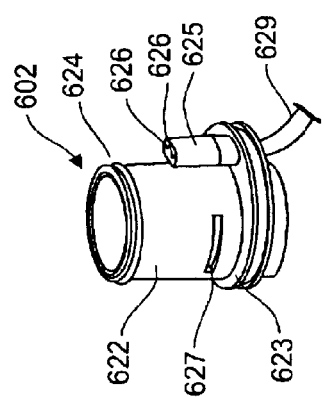
FIG. 33 is a perspective view of the male portion according to the fourth form of the connector of the present invention.

Referring to FIG. 33, which depicts the male portion 602 of the connector of the present invention: The male portion 602 is formed from a plastics type material by injection moulding, but may be formed from other appropriate materials using other appropriate methods. The male portion is generally tubular in shape to allow gases to pass there through. It has a main body 622 that has a rim 623 located near to one end of the body 622. The other end of the body 622 terminates in an attached o-ring 624 that creates a seal between the male portion 602 and the female portion 601 when in use. Where the top of the rim 623 extends out from the side of the body 622 there is a elongate protrusion 625 of the shape and size of the recess 618 formed in the female portion 601 extending out and upward from the surface of the rim 623. Within the protrusion 625 are elongate recesses 626 that receive the pins 621 when the male portion 602 is inserted within the female portion 601.

Located partway along the body 622 of the male portion 602 are two horizontal recesses, of which only one is shown in FIG. 33. The recesses 627 are shallow and located on the outer surface of the body 622, but do not extend through to the inner surface of the body 622.

In use, once the female portion 601 has been moulded to the breathing conduit 619 the sliding collar 600 is slid over the conduit and about the female portion 601. FIG. 34 shows the sliding collar only partially covering the female portion 601, whereas FIGS. 35 and 36 show the sliding collar 600 covering all of the female portion 601. To hold the sliding collar 600 in place relative to the female portion 601 the protrusion (not shown) on the inner surface of the collar 600 is received by the small protrusion 617 on the female portion. To remove the collar from the female portion 601 the user need only grip the collar at the depressions 606 and pull the collar upwards to remove it from the female portion 601. Other means of locking the collar to the female portion are envisaged, such as twisting the collar about the female portion after the collar is slid onto the female portion, or a bayonet type fitting.

When the male portion is connected to the chamber of a humidifier by appropriate means, or if it is integrally moulded with the humidifier chamber, wires 627 extend from the male portion 602 to the humidifier heater base or another power source connected to the humidifier. These wires 627 terminate within the protrusion 625 at contacts within the recesses 626 so that when the female portion is coupled with the male portion the pins 621 slide into the elongate recesses 626 and meet with the contacts forming an electrical connection between the humidifier and wires on the breathing conduit.

In use, a pneumatic connection is achieved between the male and female portion when the male portion 602 is inserted within the female portion 601 and the pivoting members 612, 613 slide along the body 622 of the male portion 602. The inside edges of the pivoting members 612, 613 have lips 628 that extend inwardly. When the sliding collar 600 is passed down over the female portion 601 the pivoting members are pushed inwards and the lips 628 are pushed into the recesses 627 on the body 622 of the male portion 602. If a pulling force is exerted upon the breathing conduit 619 the locking together of the male and female portions prevents the breathing conduit and female portion from being removed from the male portion and chamber. Furthermore, the o-ring 624 meets with the inner surface of the upper section 609 of the female portion creating a seal between the male and female portions.

Cartridge Type Humidifier and Connector

Figure 27:
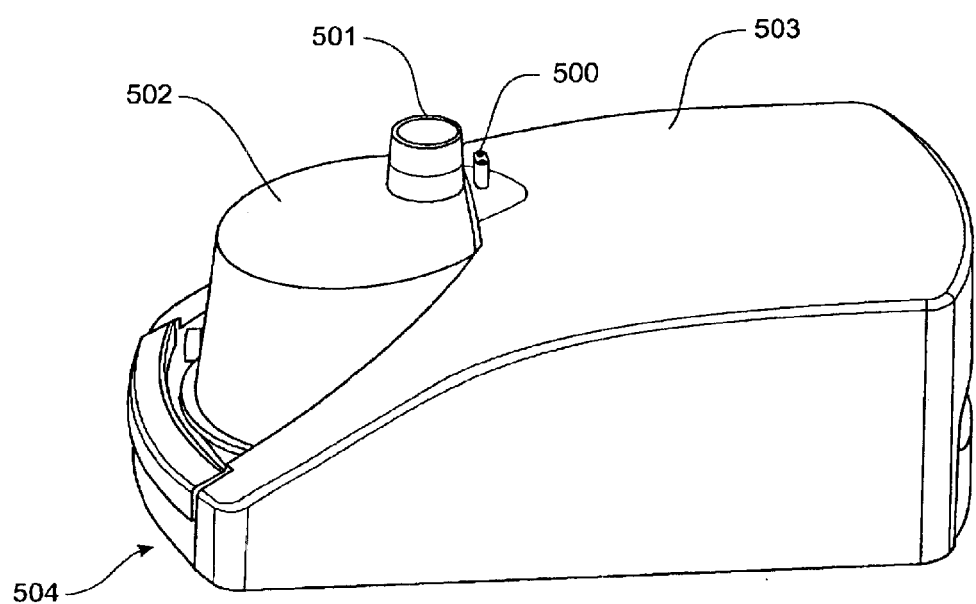
FIG. 27 is an illustration of a humidifier or CPAP device where the chamber for this device is of the cartridge type and the connector to the breathing tube is two part, the first pneumatic part located on the chamber and the second electrical part is located on the base.
Figure 28:
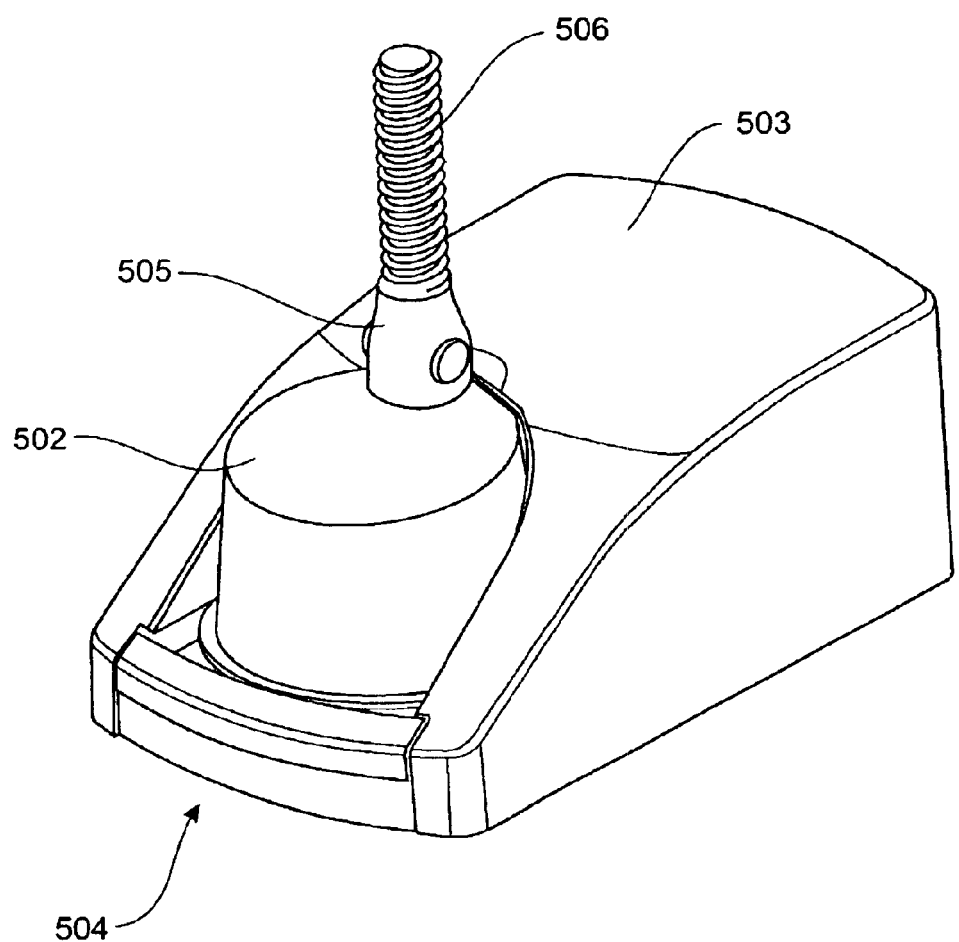
FIG. 28 is an illustration of the device of FIG. 27 when connected to the breathing tube when the breathing tube end connector extends over and about the two part connector of FIG. 27.

In other forms of the present invention, such as that shown in FIG. 27, the electrical connector part 500 of a male connector, similar to that described above, can be located on the base 503 of a humidifier 504. The humidifier 504 has a cartridge type chamber 502 which has the pneumatic connector part 501 of the male connector located on it. As shown in FIG. 28, when the female portion of the connector 505 (attached to the end of a breathing conduit 506) is connected to the male portions (both the pneumatic 501 and electrical 500 parts) the female portion 505 fits over both the pneumatic part 501 and electrical part 500 causing both a pneumatic and electrical connection to be made between the breathing conduit 506 and humidifier 504.

Dual Port Electrical/Pneumatic Connector

During use of ventilator apparatus in a hospital, where there is a humidifier and at least one breathing conduit, a connector of another preferred form of the present invention might be utilised. Some ventilator apparatus used in hospitals are provided with a dry line (dry breathing conduit) extending from the ventilator or blower that carries dry gas to the humidifier. A further breathing conduit, an inspiratory limb, extends from the humidifier to the patient and carries humidified gases to the patient. A connector that can be used with such a system will now be described.

Figure 14:
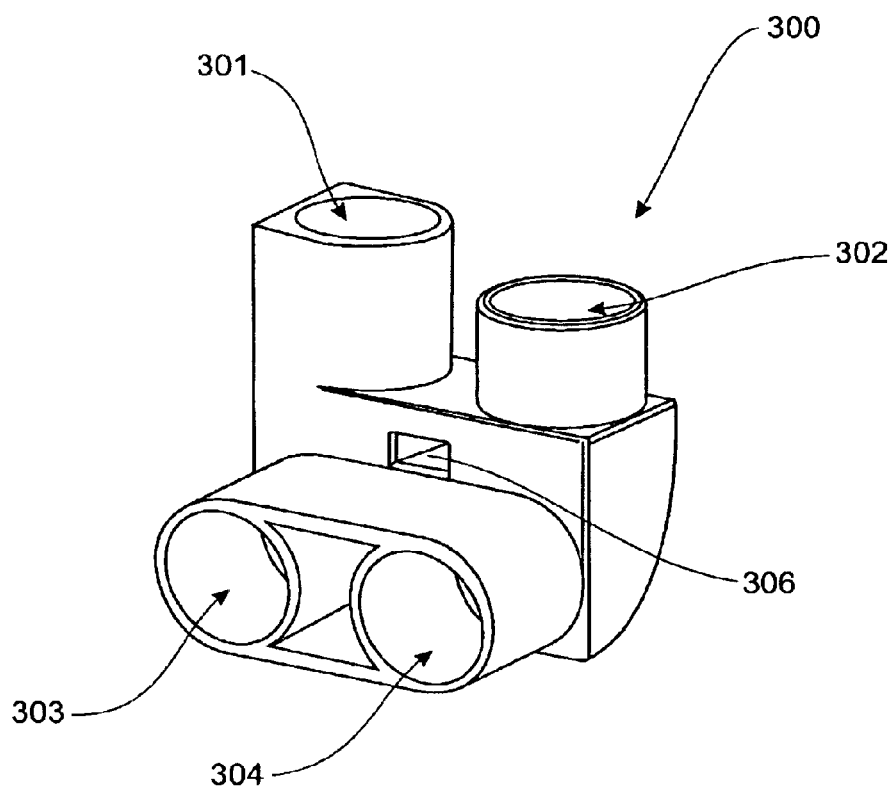
FIG. 14 is a perspective view of the male portion of a second form of the connector of the present invention, where the connector has a dual port.
Figure 15:
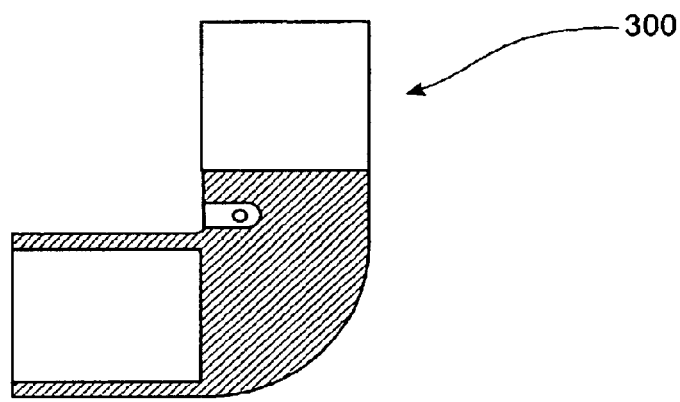
FIG. 15 is a partial cross-section side view of the male portion of the second form of the connector as shown in FIG. 12.
Figure 16:
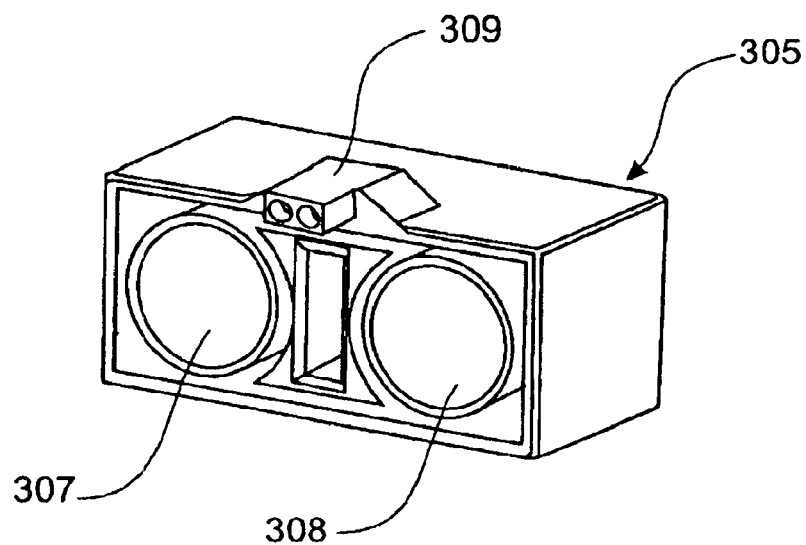
FIG. 16 is a perspective view of the female portion of the second form of the connector of the present invention.
Figure 17:
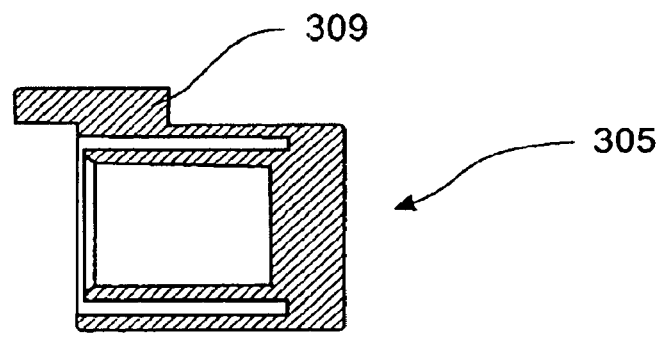
FIG. 17 is a cross-section of the female portion as shown in FIG. 15.

The male portion 300 of a dual port cartridge connector is shown in FIGS. 14 and 15. The dual cartridge connector provides two pneumatic connections, one between the dry line and the humidifier, and the other between the inspiratory limb and the humidifier. This connector also provides for an electrical connection from the humidifier to the wires residing in each of the dry line and inspiratory limb. The male portion 300 has four tubular shaped protrusions that each defines a port 301, 302, 303, 304. The first port 301 is connected to the conduit of the dry line, and the second port 302 is connected to the conduit of the inspiratory limb. The third 303 and fourth 304 tubular shaped ports are connected via a female portion 305 (as shown in FIGS. 16 and 17) to the humidifier. The male portion also has located on it a rectangular shaped recess 306 that has contacts within it that meet with the electrical wires running within or about the tubes.

To provide a pneumatic connection between each of the tubes and a humidifier the third 303 and fourth 304 ports are inserted into complementary shaped recesses 307, 308 in the female portion 305 and a latch (not shown) is inserted in a recess that causes the locking of the male and female portions together. The latch may be formed integrally with the female portion, residing approximately where the electrical protrusion 309 is located. Similarly, the recess may be integrally formed with the electrical recess 306 of the male portion. Alternatively both the latch and recess may be formed in the male and female portions at other appropriate locations. On insertion, a simultaneous electrical connection is made as the rectangular shaped electrical protrusion 309 located on the female portion 305 is inserted into the electrical recess 306 of the male portion 300. The electrical protrusion 309 is connected to wiring within the humidifier and subsequently to the control mechanisms within the humidifier, to provide power to the electrical wiring and to control the heating of the conduit, or to pick up signals sent through the wiring, similar to that as described above.

The female portion 305 may form part of the chamber of the humidifier or may be attached by appropriate means to the humidifier, similar to that of the single port form of the connector as described above in relation to FIGS. 8 to 13.

The male 300 and female 305 portions are each injection moulded. In some cases the female portion 305 may be integrally injection moulded with the humidifier chamber. Each of these portions may be formed by other appropriate methods.

A dual port connector of this type allows for the connector to be easily dismantled and cleaned. Furthermore, the connector part, being made from a plastics type material is inexpensive to manufacture and will give hospitals and patients the option to dispose of the connector rather than to clean and disinfect the connector for reuse.

We claim:

1. A connector for coupling a gases supply to a conduit, where said conduit is of the type that includes electrical wire extending within, throughout or about said conduit, said connector comprising:

a female gases passage portion of a generally tubular shape attached in use to one of said gases supply or said conduit, said female portion including a locking connector and an electrical connector, a male gases passage portion of a generally tubular shape attached in use to the other of said gases supply or said conduit, said male gases passage portion including a locking connector receiver and an electrical connector receiver, said male gases passage portion and said female gases passage portion coupled in use to form a pneumatically sealed gases passage between said gases supply and said conduit, said coupling also engaging said electrical connector and said electrical connector receiver, a collar of generally tubular shave on said female portion, said collar capable of being moved over said female gases portion once said male and female gases passage portions are coupled in use, said collar causing said locking connector to engage with said locking connector receiver to releasably lock said male and female portions together.

2. A connector according to claim 1 wherein said collar is capable of being threaded to said female gases passage portion.

3. A connector according to claim 1 wherein said locking connector receiver is at least one recess located at the external surface of said male portion, and said locking connector is at least one protrusion on the internal surface of said female gases passage portion, shaped to engage with said at least one recess to enable said releasable locking of said male and female gases passage portions together.

4. A connector according to claim 3 wherein said collar is capable of being threaded to said female gases passage portion.

5. A connector according to claim 3 wherein said collar causes said at least one protrusion to engage with said recess, said collar including at least one projection that abuts said female gases passage portion and causes said releasable locking of said male and female gases passage portions together.

6. A connector according to claim 5 wherein said collar is capable of being threaded to said female gases passage portion.

7. A connector according to claim 5 wherein said gases supply is a humidifier.

8. A connector according to claim 5 wherein said gases supply is an integrated blower and humidifier.

9. A connector according to claim 5 wherein said gases supply is a positive pressure ventilation device.

10. A connector according to claim 5 wherein said electrical connector is a protrusion located on the external surface of said male gases passage portion, said protrusion having at least one electrical contact surface and being connected to at least a power supply, and wherein said electrical connector receiver is a port located on the external surface of said female gases passage portion, sized to receive said protrusion, said protrusion making at least one electric contact with said port.

11. A connector according to claim 10 wherein said port contains at least one pin, and said protrusion contains at least one elongate recess which in use receives said at least one pin.

* * * * *